United States Patent
Aust et al.

(10) Patent No.: US 6,447,793 B2
(45) Date of Patent: *Sep. 10, 2002

(54) WATER SOLUBLE, BROAD SPECTRUM PRESERVATIVE SYSTEM

(75) Inventors: Duncan Aust, East Setauket, NY (US); Stephen Spiegelman, deceased, late of Westbury, NY (US), by Harriet Spiegelman, administrator; Michael Ross, East Setauket, NY (US)

(73) Assignee: The Collaborative Group, Ltd., East Setauket, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/396,949

(22) Filed: Sep. 15, 1999

Related U.S. Application Data

(60) Provisional application No. 60/100,541, filed on Sep. 16, 1998.

(51) Int. Cl.⁷ ............ A01N 25/00; A61K 7/00; C09K 3/00
(52) U.S. Cl. .............. 424/405; 424/401; 514/844; 252/380
(58) Field of Search ................ 424/401, 405; 514/844; 252/380

(56) References Cited

U.S. PATENT DOCUMENTS

| | | | | |
|---|---|---|---|---|
| 5,490,992 A | | 2/1996 | Andrews | |
| 5,656,591 A | | 8/1997 | Tomita | |
| 5,658,580 A | * | 8/1997 | Mausner | 424/401 |
| 6,120,758 A | * | 8/1997 | Siddiqui et al. | 424/78.02 |
| 5,670,160 A | | 9/1997 | Eggensperger | |
| 5,885,596 A | * | 3/1999 | Parab | 424/401 |
| 5,902,591 A | * | 5/1999 | Herstein | 424/401 |
| 5,980,970 A | * | 11/1999 | Sattler et al. | 426/611 |
| 6,036,946 A | * | 3/2000 | Greene | 424/59 |

\* cited by examiner

*Primary Examiner*—José G. Dees
*Assistant Examiner*—Marina Lamm
(74) *Attorney, Agent, or Firm*—Darby Darby

(57) ABSTRACT

An effective broad spectrum system useful in an extended range of physical factors and/or composition elements in a cosmetic or personal care product for preservation is described by the present invention. The broad spectrum, water soluble preservative system of the present invention includes an acid or acid derivative, chlorphenesin and a solvent mixed with phenoxyethanol.

6 Claims, 8 Drawing Sheets

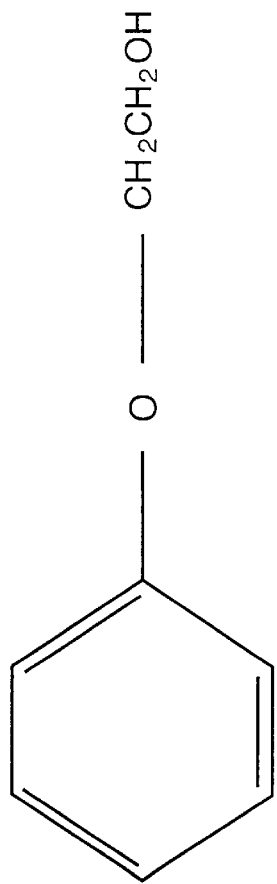
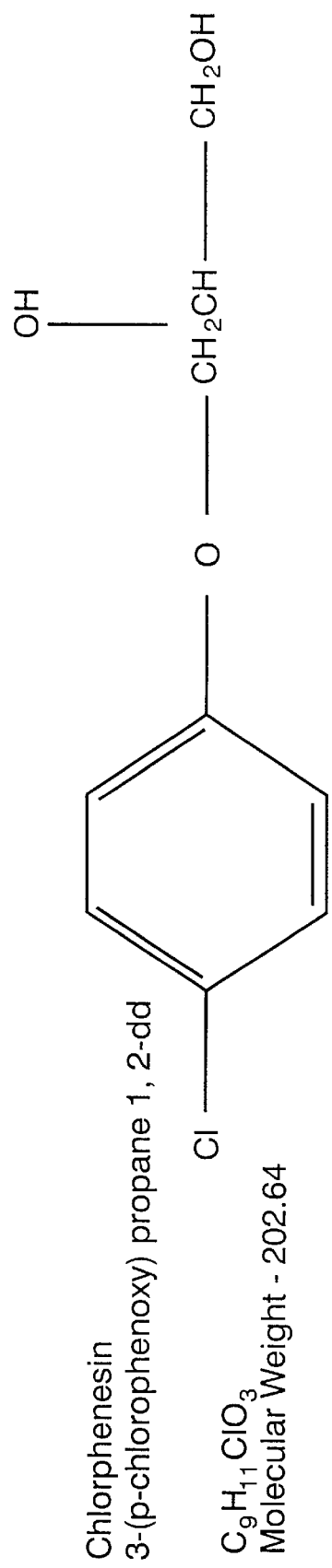
Figure 1a
Phenoxyethanol
$C_8H_{10}O_2$
Molecular Weight - 138.16
Figure 1b
Chlorphenesin
3-(p-chlorophenoxy) propane 1, 2-dd
$C_9H_{11}ClO_3$
Molecular Weight - 202.64

WATER SOLUBLE, BROAD SPECTRUM PRESERVATIVE SYSTEM

CROSS-REFERENCE TO RELATED APPLICATION

This is a non-provisional patent application of U.S. Provisional Application Ser. No. 60/100,541 filed Sep. 16, 1998 now abandoned.

BACKGROUND OF THE INVENTION

The present intention relates to preservative systems. More particularly, this invention relates to a water soluble, broad spectrum preservative system for effectively inactivating water-borne microorganisms in formulations which may differ significantly in composition.

Conventional preservative systems are typically included in personal care products, cosmetic formulations, etc., which include an aqueous phase. Water is required for growth of microorganisms. Since water is an ingredient in many personal care products and cosmetic formulations, they are susceptible to microbial action. Cosmetic and/or other personal care products which do not contain water, that is anhydrous products, do not require extensive preservation to maintain. Microorganisms of general concern to formulators include bacteria (enterics, pseudomonads, staphylococci) yeasts and molds. Microorganisms may require specific environmental conditions to grow. Variations n the physical and chemical state of different compositions enhance or impede microbial growth.

Preservatives and preservative systems known for use against a range of microorganisms are classified as "broad spectrum" preservatives because they are intended to control multiple organisms, such as some combination of the five categories mentioned herein. Conventional preservatives are not typically broad spectrum. They are usually directed to prevent or diminish the growth of one or two of the categories mentioned. Further, various elements known which might be used to control a broad spectrum of microorganisms mentioned, tend to be restricted by limited solubility in water. That is, limited solubility prohibits some constituents from being used in preservative product systems formulated with modest to large amounts of water.

Known broad spectrum antimicrobial systems are limited to specific applications. For example, U.S. Pat. No. 5,670,160 discloses a preservative system meant for use in compositions having an aqueous phase which comprises three (3) components: (1) an organic acid, or salt of same, (2) a monophenyl glyycol ether, and (3) at least one poly (hexamethylenebiguanide) salt, or salt or other guanidine derivative. The '160 patented preservative system displays broad spectrum antimicrobial activity when used at low concentrations. The formulation is known to be used in formulations such as shampoos, creams, lotions and for products in the field of detergents and cleaners. However the '160 patented system is not suitable in formulations used in skin sensitive applications.

Another example of a prior art attempt to realize a broad spectrum antimicrobial is disclosed in U.S. Pat. No. 5,656,591. The antimicrobial agent of the '591 patent includes one or more antimicrobial peptides derived from lactoferrins, and including one or more compounds selected from a group of metal-chelating tocophenol, cyclodextrin, glycerin-fatty acid ether alcohol, EDTA or salts thereof, ascorbic acid or a salt thereof, citric acid or a salt thereof, polyphosphoric acid or a salt thereof, chitosan acid, cysteine and cholic acid. Comparable to the '160' patented system described above, the 591 patented system is not useable in skin-sensitive applications. Further, U.S. Pat. No. 5,490,992 discloses a product and process for reducing microbial contamination by pathogenic or other undesired bacteria by way of a fatty acid monoester mixed with an acid or chelating agent, and a food grade surfactant. The three component formulation provides effective antimicrobial activity synergistically by use of the three components together. For that matter, any of the components recited in the '992 system would not be effective without the other two components to ensure required antimicrobial activity. That is, without the specific combination and concentration of the components in the formulation, the patent asserts that it would not be possible to control microbial growth.

Such formulations would be capable of controlling growth, but would require high concentrations which could adversely affect the organoleptic characteristics of the formulation.

It is believed that the shortcomings mentioned, re prior art preservation systems for use in cosmetics and/or personal care products containing water, relate to the known fact that the effectiveness of water-based antimicrobials varies with pH and other characteristics of the formulation system. Various other preservative are known to be effective under particular conditions, but insufficient to guarantee antimicrobial activity for a broad class of microorganisms. For example, phenol derivatives such as orthophenylphenol, chloroxylenol and resorcinol are used in personal care products but only in very limited quantities because of possible toxicity to humans. The industry is more likely to use ring-substituted derivatives of phenol, relying on its inherent property that the more lipophilic the phenol entity, the greater its antimicrobial activity.

It is another object of the present invention to provide a multiple ingredient, broad-spectrum preservative system displaying an effectiveness which exceeds a summation of the ingredients individually, in a synergistic manner.

In a preferred embodiment, the broad-spectrum water soluble preservative system of the present invention includes an acid or acid derivative (benzoic acid, sorbic acid, esters of parahydroxybenzoic acid, etc) chlorphenesin, a solvent (alcohol, propylene glycol, butylene glycol, glycerine) mixed with phenoxyethanol. A synergy between the elements comprising the invention occurs resulting in an effective broad spectrum preservative system useful in an extended ranges of physical attributes and chemical compositions of cosmetic or personal care products.

An acceptable range of phenoxyethanol in the broad-spectrum water soluble preservative system of the present invention is 40 to 85 percent. An acceptable range of the solvent component is 2 to 48 percent; an acceptable range of the acid or acid derivative is 2 to 20 percent, and an acceptable range of chlorphenesin is added in an amount of 10 to 30 percent to prepare the broad-spectrum water soluble preservative system of the present invention. The resulting preservative system may be used at levels of 2 percent or less as an effective antimicrobial in various products, to be discussed in further detail below.

DETAILED DESCRIPTION OF THE INVENTION

The effectiveness of the broad spectrum antimicrobial preservative system of the present invention is a result of the synergistic antimicrobial effect of the four constituents which comprise the system. That is, the broad spectrum preservative of this invention includes phenoxyethanol, a glycol solvent, an acid or acid derivatives and chlorphenesin in varying amounts, whereby 2 percent or less of the system in a product by weight is effective. The synergistic effect of the combination of the four separate components realizes broad spectrum antimicrobial range. However, it should be noted that each of the four ingredients of the invention may display antimicrobial activity when acting alone.

Minimum inhibitory concentrations (MIC) were determined for Germazide WS and Germazide MPB using inocula of gram negative rods, gram positive rods, yeast and mold. The MIC is defined as the lowest concentration of test agent inhibiting visible growth.

All percents by weight are based upon the total preservative composition weight.

A cosmetic composition comprises up to 2% by weight of the preservative of the invention; and up to 98% by weight of inert non-toxic topically acceptable carrier ingredients suitable for topical application to the skin of a warm-blooded animal, such as a person. Here all percents by weight are based upon the total cosmetic composition weight.

REAGENTS FOR GERMAZIDE™ (WS and MPB)

| Material | Source | City | State/Country |
|---|---|---|---|
| Chlorphenesin | Kraemer | Hamburg | Germany |
| Phenoxyethanol | Universal | S. Edison | New Jersey |
| Sorbic acid | Spectrum | Gerdena | California |
| Benzoic Acid | Ruger | Irvington | New Jersey |
| Methyl paraben | Universal | S. Edison | New Jersey |
| Glycerine | Kramer | Clifton | New Jersey |
| Propylene Glycol | Kramer | Clifton | New Jersey |

The adequacy of preservation of Germazide compositions was determined by challenging a variety of formulations with specific microorganisms. The test formulation was inoculated to a final concentration of one million to ten million bacteria and one hundred thousand to one million yeast and mold. The number of surviving organisms was determined at 7, 14, 21 and 28 days. Following the 14 day count, the formulation was reinoculated to determine the effect of microbial stress on the preservative system.

Phenoxyethanol, in particular, or phenol derivatives in general (collectively "phenols), while one of the four ingredients in the present invention are infrequently used as preservatives in cosmetics or personal care products, phenols are typically used as disinfectants and in large amounts can be toxic to humans. A significant factor in projecting or determining phenol antimicrobial activity in a compound, particularly compounds which contain oil/water phases, lies in the degree of partitioning between the two phases.

That is, in compositions composed of separate phases, e.g, oil and water, the relationship between the phases is a significant factor or parameter for determining antimicrobial activity in phenolic compounds. Specifically, lipophilic compounds display antibacterial activity as a result of the compound's compulsion to partition into lipid containing bacterial membranes. Phenyl derivatives appear to function at low concentrations by disrupting the proton motive force, as do parabens.

Several alcohols are known to be useful as preservatives in cosmetic applications. For example, ethanol or ethyl alcohol is typically used around 15 percent of the total formula weight. Propylene glycol, an alcohol, is used to potentiate the antimicrobial activity of the Parabens. Phenoxyethanol, an alcohol also known as ethylene glycol monophenyl ether, is also used to preserve hydrous formulations, with similar drawbacks as those mentions above.

Sorbic acid is known for use as an antimicrobial Sorbic acid is a straight-chain unsaturated fatty acid, the potassium salt of which is water soluble. Typically, sorbic acid salts are incorporated into formulations as a preservative additive. The pH of the formulation is decreased to release free sorbic acid from the salt, the resulting sorbic acid acting as a preservative in the formulation, at the stated activity level. Usefulness of sorbic acid, and therefore, the antimicrobial activity that sorbic acid brings to a formulation is pH dependent. That is, sorbic acid is effective in formulations displaying pH of 4.5 or lower. Once the pH increases above 4.5, its activity is curtailed. At pH of 4.5 or below, sorbic acid is found to be very active against mold, fair against yeast and poor against most bacterial. A first embodiment of the invention includes a water-soluble, broad spectrum preservative system (Germazide™ WS) for use in water-based cosmetic products to control microbiological growth in same products. The system comprises: approximately forty (40) to 85 weight percent of phenoxyethanol; approximately two (2) to forty-eight (48) weight percent of a solvent; approximately two (2) to ten (10) weight percent of an acid or its derivatives; and approximately ten (10) to thirty (30) weight percent of chlorphenesin.

Preferably, the broad spectrum, water-soluble preservative system is defined wherein the weight percent of phenoxyethanol is sixty (60), the weight-percent of propylene glycol is fifteen (15), the weight percent of sorbic acid is five (5) and the weight percent of chlorphenesin is twenty (20). It should also be noted that weight percentages of the broad spectrum water soluble-preservative in the products in which it is used is not greater than two (2) percent.

A second embodiment of the invention includes a water-soluble, broad spectrum preservative system (Germazide™ MPB) for use in water-based cosmetic products to control microbiological growth in same products. The system comprises approximately forty (40) to 85 weight percent of phenoxyethanol; approximately two (2) to thirty-eight (38) weight percent of glycerine; approximately two (2) to ten (10) weight percent benzoic acid; and approximately two (2) to ten (10) weight percent parahydroxybenzoic acid esters (parabens); and approximately ten (10) to thirty (30) weight percent of chlorphenesin.

Preferably, the broad spectrum, water-soluble preservative system is defined wherein the weight percent of phenoxyethanol is 56, the weight-percent of glycerine is fifteen (15), the weight percent of benzoic acid is six (6), the weight percent of methyl paraben is seven (7) and the weight percent of chlorphenesin is sixteen (16). It should also be noted that weight percentages of the broad spectrum water soluble-preservative in the products in which is used is not greater than two (2) percent.

OBJECTS AND SUMMARY OF THE INVENTION

It is an object of the present invention to overcome the shortcomings of broad spectrum preservative systems known in the art.

It is another object of the present invention to provide a broad spectrum, water soluble, preservative system which may be effectively used in a broad range of pH.

BRIEF DESCRIPTION OF THE DRAWINGS

Other objects and features of the present invention will become apparent from the following detailed description considered in connection with the accompanying drawings which disclose several embodiments of the present invention. It should be understood, however, that the drawings are designed for the purpose of illustration only and not as a definition of the limits of the invention.

In the drawings, FIGS. 1a and 1b show chemical structures;

Figure 2:
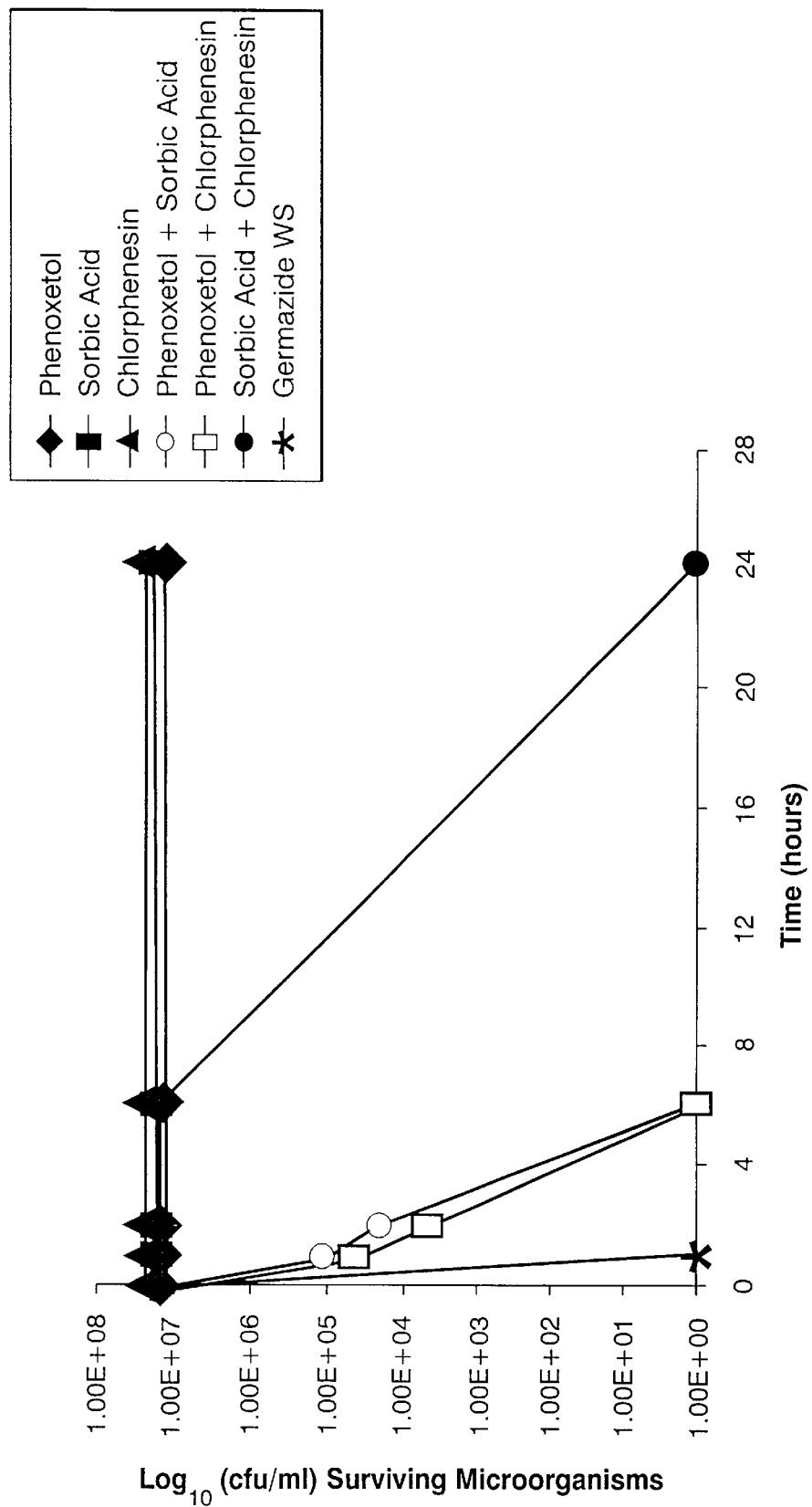
FIG. 2 shows bactericidal effect of Germazide™ active ingredients on *Escherichia coli* at 1% use level.

Specific embodiments of the present invention are illustrated in the following examples. It will be understood however, that the invention is not confined to the specific limitations set forth in the individual examples, but rather to the scope of the appended claims. All examples listed below passed full CTFA challenge test protocols with less than 10 cfu's recovered in all pools.

EXAMPLE 1

An Oil-Free Cream/Gel was prepared as follows:

| Ingredient | % w/w |
| --- | --- |
| Deionized Water | 87.65 |
| Titanium Dioxide | 0.20 |
| Carbomer | 0.65 |
| Glycerin | 3.00 |
| Sorbitol 70% | 4.00 |
| Dimethicone Copolyol | 0.50 |
| PEG-20 | 1.20 |
| Chamomile Extract | 1.00 |
| Fragrance | 0.20 |
| Triethanolamine 99% | 0.50 |
| Disodium EDTA | 0.10 |
| Germazide WS | 1.00 |
| | 100.00 |

EXAMPLE 2

A non-ionic emulsion was prepared as follows:

| Ingredient | % w/w |
| --- | --- |
| Deoinized Water | 70.50 |
| Xanthan Gum | 0.05 |
| Glycerin 99.7% | 5.50 |
| Sodium Hyaluronate | 0.05 |
| Tetrasodium EDTA | 0.10 |
| Octyldodecyl Stearoyl Stearate | 1.50 |
| Propylene Glycol Dicaprylate/Dicaprate | 3.00 |
| PPG-15 Stearyl Ether | 1.00 |
| Cetearyl Alcohol | 3.00 |
| Glyceryl Stearate | 3.50 |
| Hydrogenated Polyisobutene | 1.00 |
| Sesame Oil | 1.00 |
| Dimethicone, 100 cSt. | 0.20 |
| Hydrogenated Vegetable Oil | 5.50 |
| PEG-100 Stearate | 1.90 |
| Steareth-2 | 0.80 |
| Carbomer | 0.10 |
| Triethanolamine 99% | 0.30 |
| Germazide WS | 1.00 |
| | 100.00 |

EXAMPLE 3

A cationic hair condition was prepared as follows:

| Ingredient | % w/w |
| --- | --- |
| Deionized Water | 67.95 |
| Xanthan Gum | 0.30 |
| Cellulose Gum | 0.05 |
| Aloe Barbadensis Gel | 4.00 |
| Glycerin 99.7% | 5.00 |
| Algae Extract | 5.00 |
| Citric Acid, USP | 0.05 |
| Hydrogenated Vegetable Oil | 5.00 |
| Avocado Oil | 2.00 |
| Cetyl Alcohol | 4.00 |
| Behentrimonium Methosulfate (and) Cetearyl Alcohol | 2.75 |
| PEG-100 Stearate | 1.50 |
| Steareth-2 | 0.70 |
| Tocopheryl Acetate | 0.50 |
| Fragrance | 0.20 |
| Germazide WS | 1.00 |
| | 100.00 |

EXAMPLE 4

An anionic Shampoo was prepared as follows:

| Ingredient | % w/w |
| --- | --- |
| Deionized Water | 54.65 |
| Sodium Laureth Sulfate, 25% | 30.00 |
| Cocamidopropyl Betaine, 35% | 8.00 |
| Cocamide MEA | 3.25 |
| PEG-150 Distearate | 0.50 |
| Glycol Stearate | 1.50 |
| Polysorbate 20 | 1.00 |
| Fragrance | 0.10 |
| Germazide WS | 1.00 |
| | 100.00 |

EXAMPLE 5

A low-pH (3.50), non-ionic emulsion was prepared as follows:

| Ingredient | % w/w |
| --- | --- |
| Deionized Water | 82.65 |
| Xanthan Gum | 0.10 |
| 1,3 Butylene Glycol | 1.00 |
| Disodium EDTA | 0.10 |
| Mixed Fruit Acids | 2.00 |
| Hydrogenated Vegetable Oil | 2.00 |
| Cyclomethicone | 2.50 |
| Dimethicone, 100 cSt. | 1.50 |
| Glyceryl Stearate | 2.00 |
| Cetyl Alcohol | 1.00 |
| Glyceryl Stearate (and) PEG-100 Stearate | 1.20 |
| Steareth-2 | 0.60 |
| PEG-100 Stearate | 0.80 |
| Polyacrylamide (and) C13–14 Isoparaffin (and) Laureth-7 | 1.50 |
| Fragrance | 0.05 |
| Germazide WS | 1.00 |
| | 100.00 |

EXAMPLE 6

An aqueous extraction of Green Tea was prepared as follows:

| Ingredient | % w/w |
| --- | --- |
| Deionized Water | 93.50 |
| Green Tea Pellets | 5.00 |
| Germazide WS | 1.50 |
| | 100.00 |

All the formulations listed were challenged with the following organisms: *Escherichia coli* ATCC No. 8739, *Klebsiella pneumoniae* ATCC No. 1383, *Klebsiella pneumoniae* ATCC No. 10031, *Enterobacter gergoviae* ATCC No. 33028, *Pseudomonas aeruginosa* ATCC No. 9027, *Pseudomonas stutzeri* ATCC No. 17588, *Pseudomonas putida* ATCC NO. 49128, *Pseudomonas cepacia* ATCC No. 25416, *Staphylococcus aureus* ATCC No. 6538, *Staphylococcus epidermidis* ATCC No. 12228, *Candida albicans* ATCC No. 10231, *Candida parapsilosis* ATCC No. 34136, *Aspergillus niger* ATCC No. 16404.

All the formulations tested demonstrated the broad spectrum preservative capabilities of the compositions of the present invention. Specifically, following the incubation periods described above, each formulation passed full CTFA challenge test protocols with less than 10 cfu's recovered in all pools.

The preservatives Germazide (WS) and Germazide (MPB) have the following properites: Effectiveness in killing a broad spectrum of microorganisms, ingredients having world-wide approval, low toxicity and cost and compatibility with a wide range of cosmetic ingredients. Chlorphenesin, sorbic acid and phenoxyethanol were selected, based on these attributes, and formulated in a propylene glycol base (Germazide WS). For formulators desiring compatibility with glycerin, Germazide MPB was developed, consisting of chlorphenesin, benzoic acid, Phenoxetol (phenoxyethanol) and methyl paraben in a glycerin base. Methyl paraben was added to improve control of yeast and mold contaminants. We have effectively preserved over 200 formulations with Germazide including creams, lotions, shampoos and hair conditions. The specifications for Germazide WS and Germazide MPB are shown in Table 1. The structural formulae of phenoxyethanol and chlorphenesin are shown in FIGS. 1a and 1b, respectively.

TABLE 1

Germazide Specifications

| | Typical Value | |
| --- | --- | --- |
| Property | Germazide WS | Germazide MPB |
| Color | Colorless to pale straw | Colorless to pale straw |
| Physical form | Transparent liquid | Transparent liquid |
| Specific gravity | 1.105–1.145 | 1.120–1.220 |
| Phenoxyetnanol | 54.0% | 53.2% |
| Chlorphenesin | 18.0% | 16.1% |
| Sorbic Acid | 4.5% | — |
| Benzoic Acid | — | 5.8% |
| Shelf life | 6 months (pending stability data) | 6 months (pending stability data) |
| Storage | RT in dry place, avoid temp >30° C. Do not freeze | RT in dry place, avoid temp >30° C. Do not freeze |
| Solubility | | |
| Water | 1.5% | 2.0% |
| Glycerin | >50% | >38% |
| Ethanol | >38% | >38% |
| Propylene gycol | >41% | >38% |
| Processing temp. | ≦70° C. | ≦70° C. |
| Max use in finished products | 1.5% w/w | 1.85% w/w |
| Compatibility | Non-ionic, cationic and anionic surfactants | Non-ionic, cationic and anionic surfactants |
| pH | 3.10 (1.5% ag.) | 3.06 (2% aq.) |

Following tests were conducted to assess the antimicrobial properties of formulations containing Germazide (WS) and Germazide (MPB) were evaluated for antimicrobial properties by three test procedures: Minimum inhibitory concentration (MIC), kill rate in suspension and preservative effectiveness in test formulations. MIC is defined as the lowest concentration of test agent inhibiting visible growth. The kill rate in suspension is a measure of the time in hours required to kill a suspension of microorganisms exposed to a particular concentration of the test article. Preservative effectiveness was determined by microbial challenge of the test material using the CTFA method[1].

MIC Test Method

Stock solutions of Germazide WS or Germazide MPB were serially diluted, two-fold in Tryptic soy broth (TSB). Fifty μL of culture was added to each tube containing 5 ml of the preservative-TSB dilution. Tubes were incubated and observed for growth. Results are shown in Table 2.

TABLE 2

Minimum Inhibitory Concentrations (MIC)

| Organism | ATCC No. | % w/w Germazide WS | % w/w Germazide MPB |
| --- | --- | --- | --- |
| *Escherichia coli* | 8739 | 0.5 | 0.5 |
| *Enterobacter gergoviae* | 33028 | 0.7 | 0.6 |

TABLE 2-continued

Minimum Inhibitory Concentrations (MIC)

| Organism | ATCC No. | % w/w Germazide WS | % w/w Germazide MPB |
|---|---|---|---|
| Pseudomonus aeruginosa | 9027 | 0.7 | 0.6 |
| Staphylococcus aureus | 6538 | 0.5 | 0.6 |
| Candida albicans | 10231 | 0.5 | 0.6 |
| Aspergillus niger | 16404 | 0.4 | 0.4 |

Kill Rate in Suspension

Figure 3:
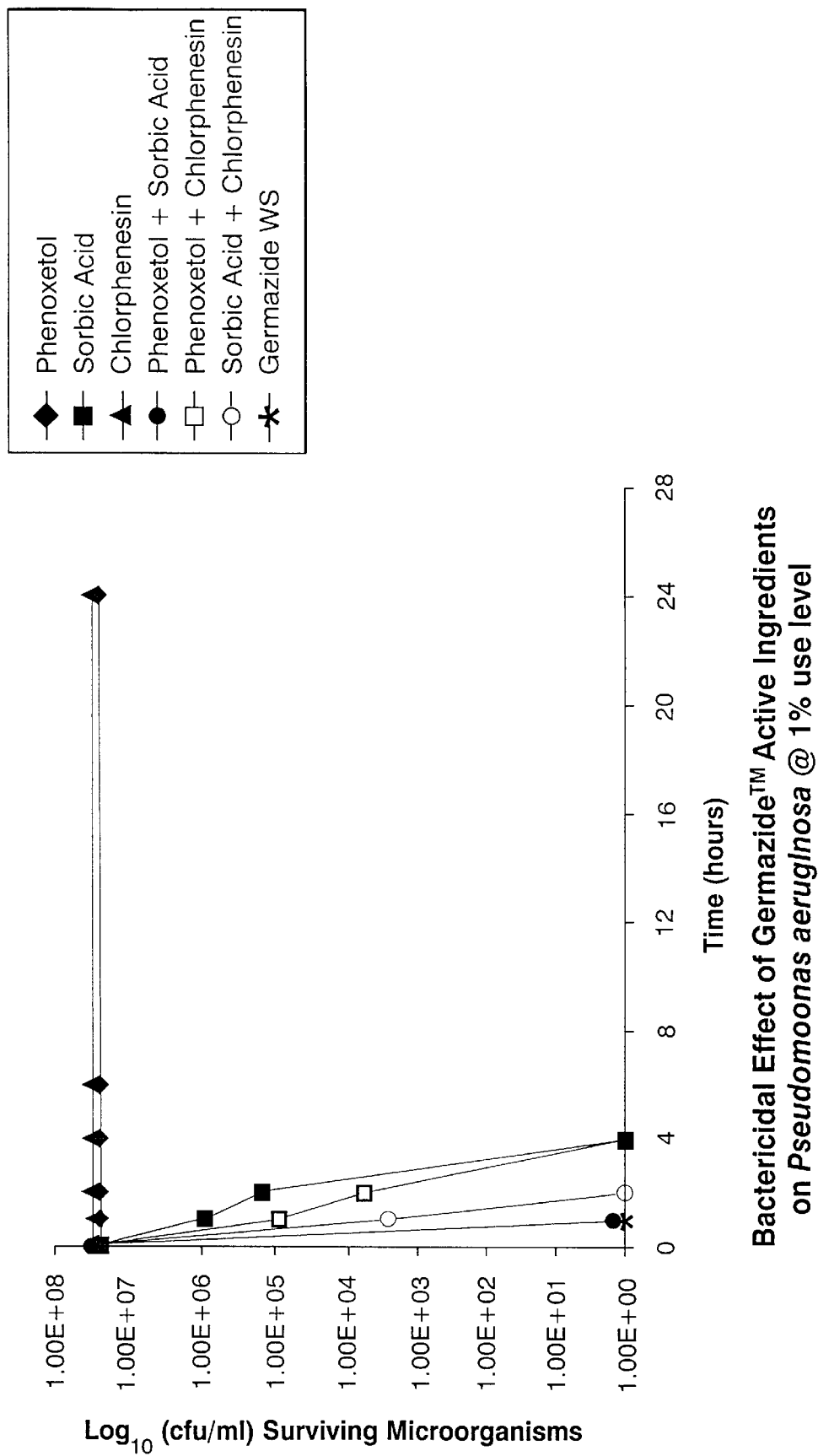
FIG. 3 shows bactericidal effect of Germazide™ active ingredients on *Pseudomonas aeruginosa* at 1% use level.
Figure 4:
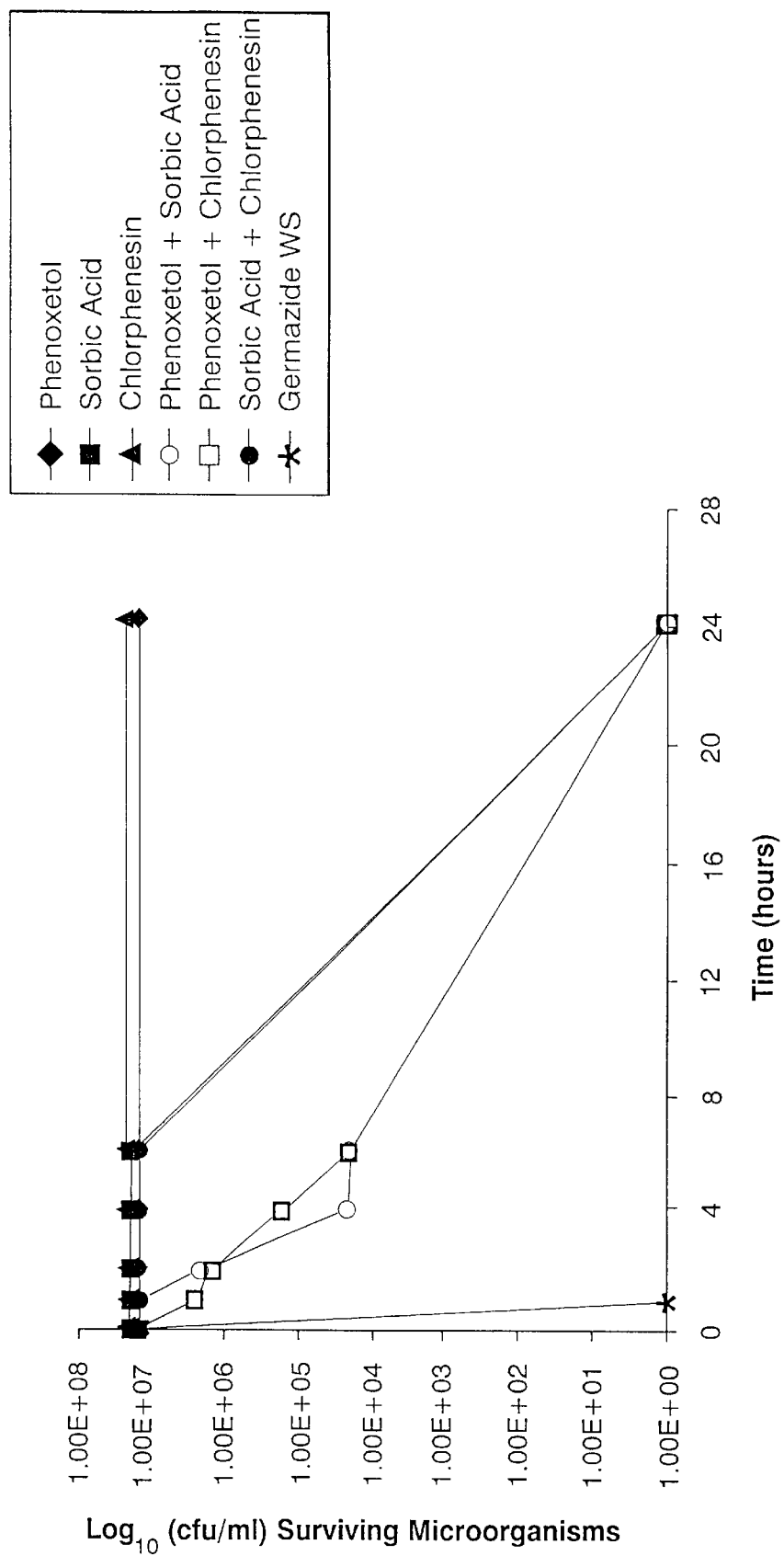
FIG. 4 shows bactericidal effect of Germazide™ active ingredients on *Staphylococcus aureus* at 1% use level.
Figure 5:
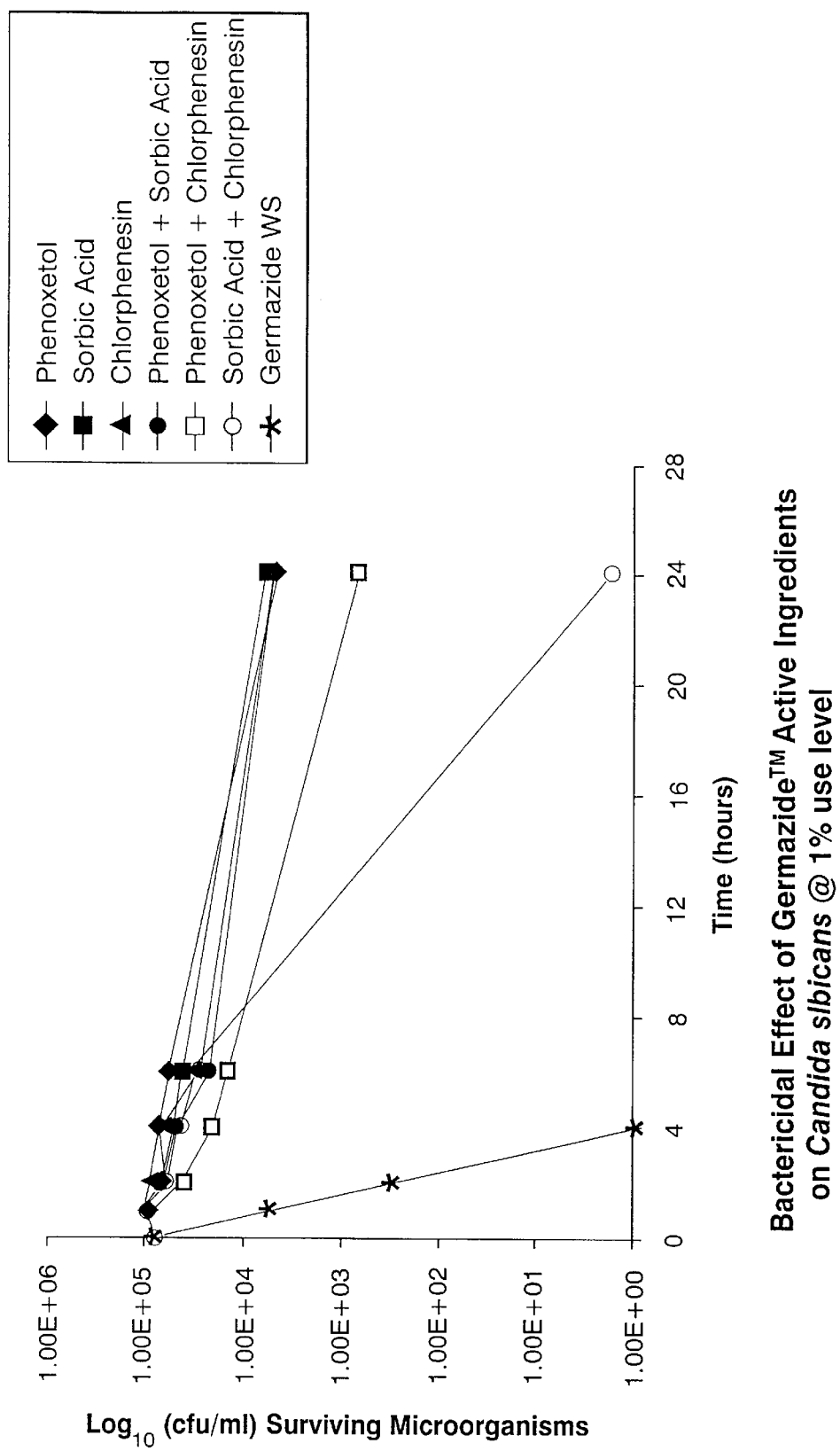
FIG. 5 shows bactericidal effect of Germazide™ active ingredients on *Candida albicans* at 1% use level.
Figure 6:
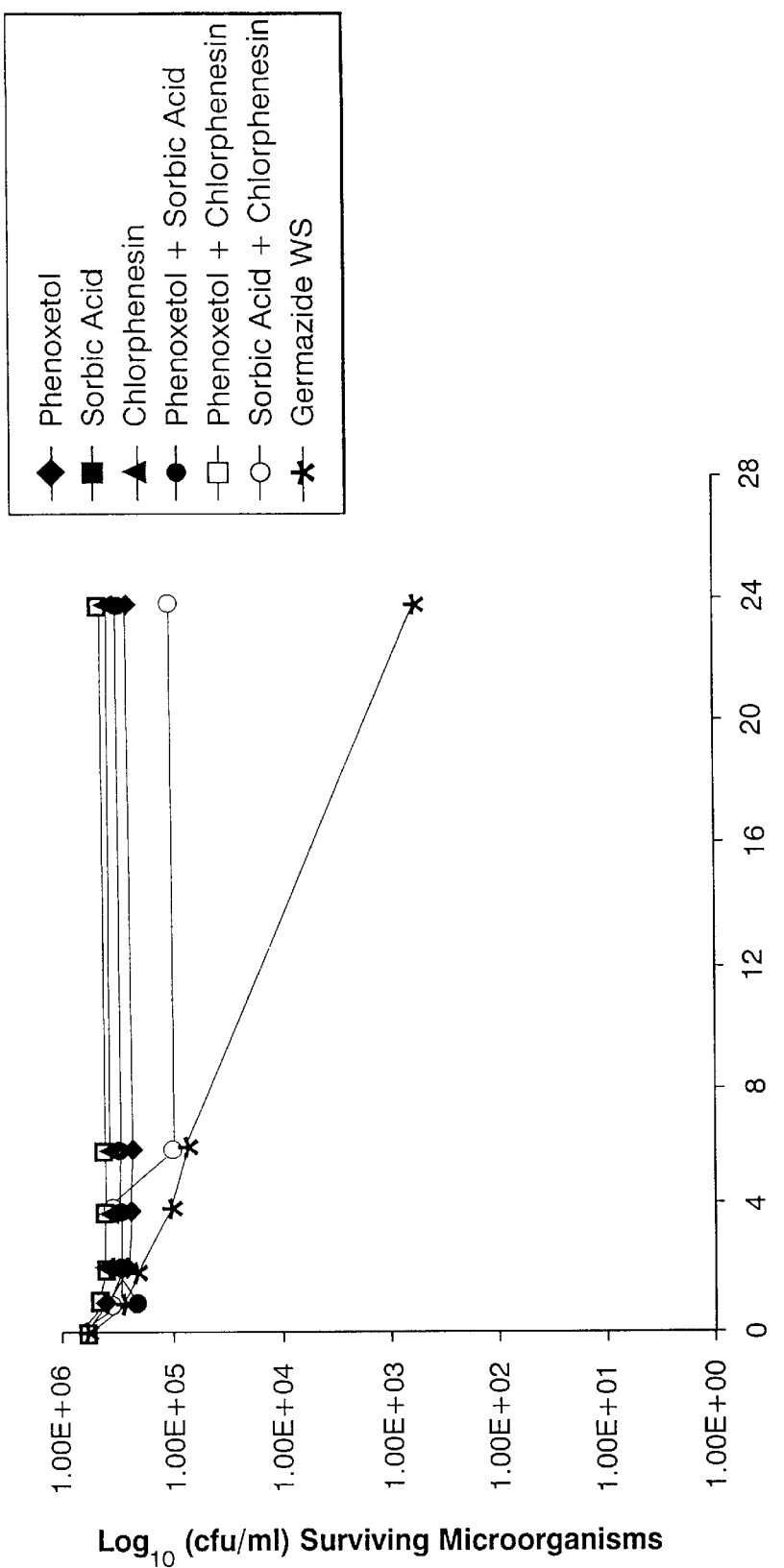
FIG. 6 shows bactericidal effect of Germazide™ active ingredients on *Aspergillus niger* at 1% use level.
Figure 7:
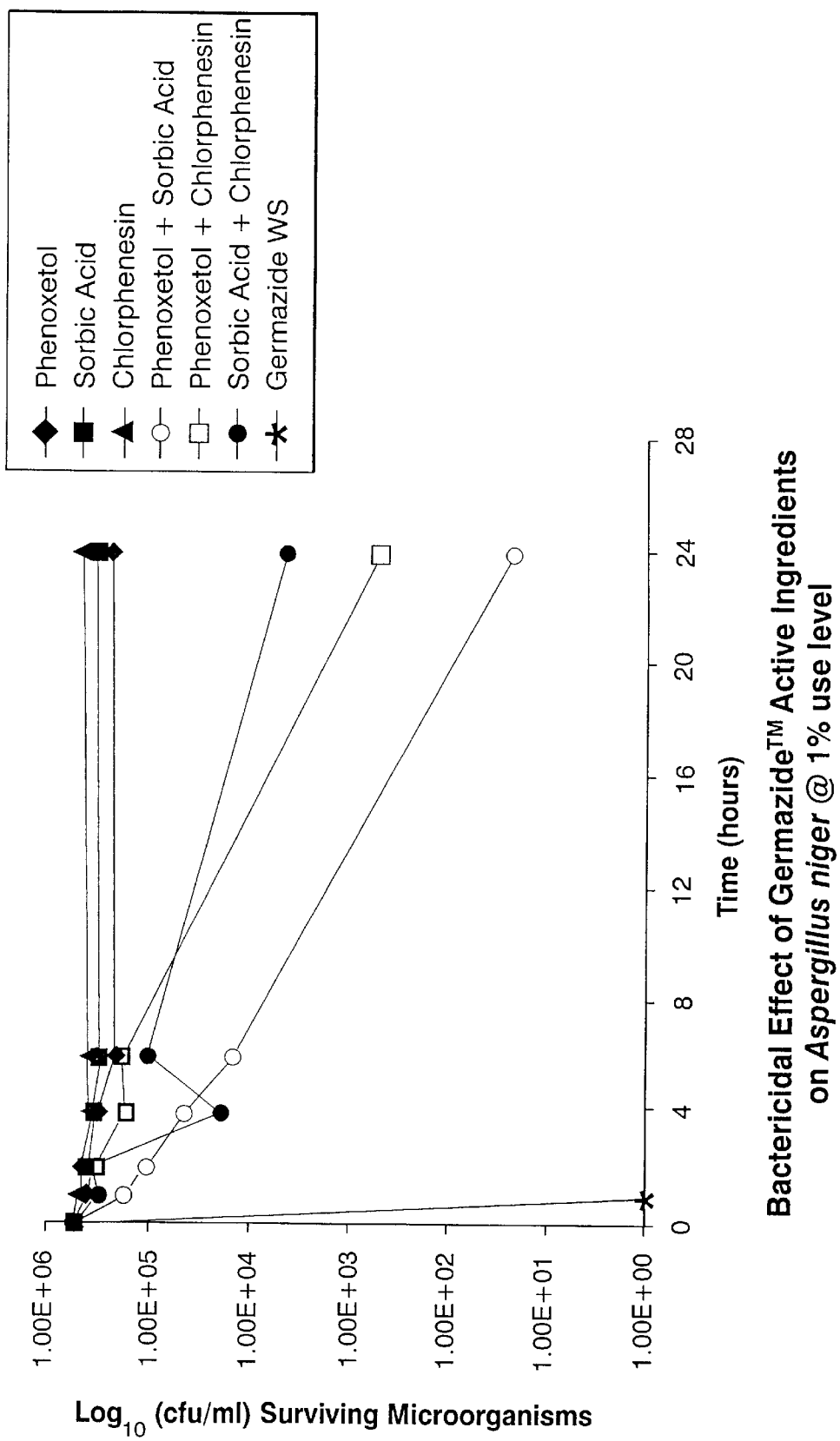
FIG. 7 shows bactericidal effect of Germazide™ active ingredients on *Aspergillus niger* at 2% use level.
Figure 8:
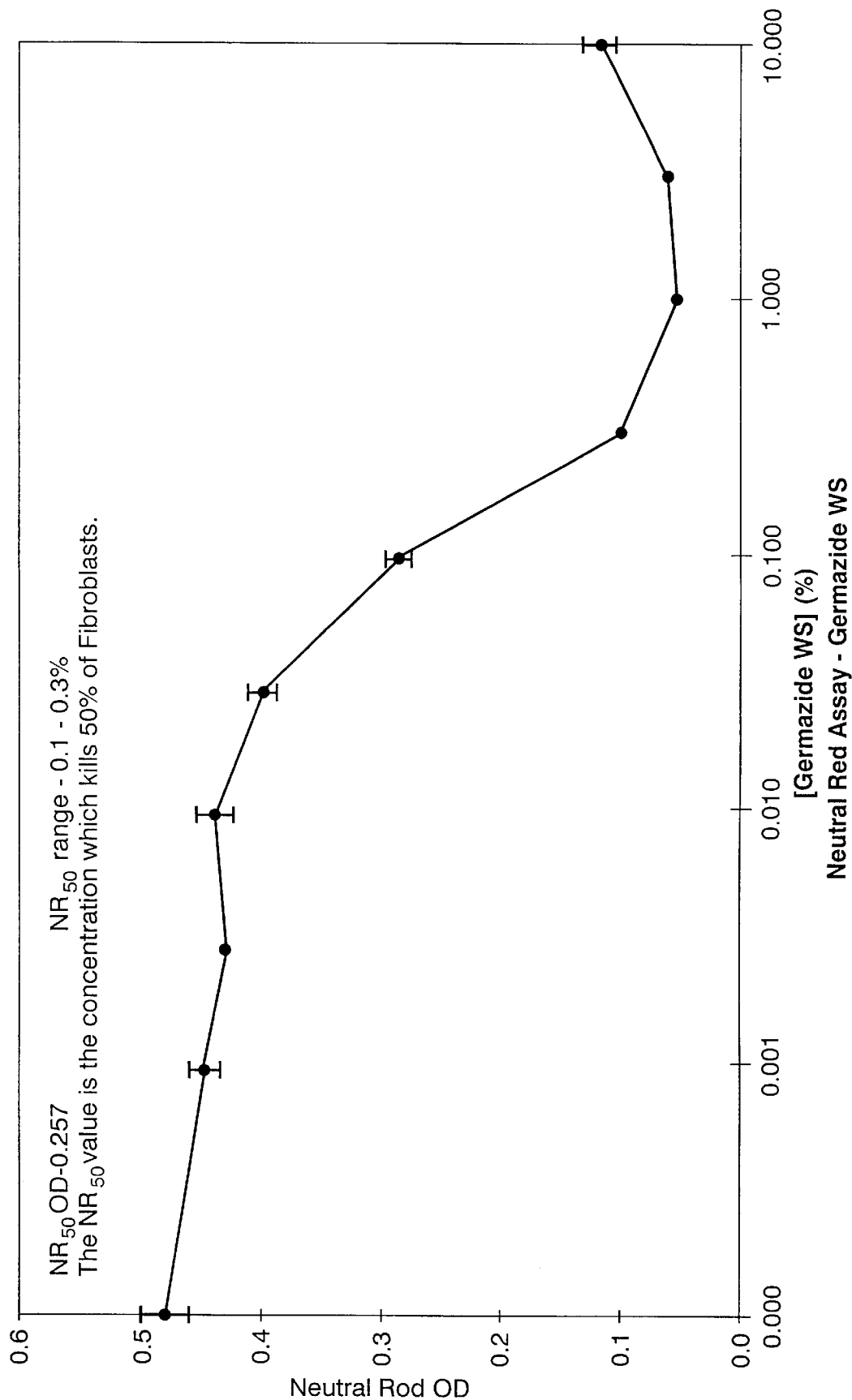
FIG. 8 shows the concentration of preservative that kills 50% of human dermal fibroblasts ($NR_{50}$).

Germazide components were prepared at the 1-% use level and each component was challenged with an overnight suspension of the bacterial or yeast test organism. A mold suspension was prepared in advance for the mold inoculum. After 0, 1, 2, 4, 6 and 24 hours, an aliquot was removed, neutralized in diluent, D/E neutralizing broth, pour-plated in Tryptic soy agar (TSA) or potato dextrose agar (PDA) and incubated. The number of surviving organisms was determined for each Germazide component. Results are shown in FIGS. 2–7.

CTFA Challenge testing

Test formulations were challenged with from one hundred thousand to ten million cfu's test organism pool per gram or ml of sample at zero time and two weeks. The number of surviving organisms was determined at 1, 2, 3 and 4 weeks. Results of two representative test formulations are shown in Table 3.

TABLE 3

Challenge Tests (CTFA Microbiology Guidelines, M-3, Number of surviving organisms (cfu/g) after DAYS:

| # of Days Organism | 0 Inoc. | 7 Count | 14 Count | 14 Inoc. | 21 Count | 28 Count |
|---|---|---|---|---|---|---|
| Formulation: All Purpose Cream Preservative: Germazide WS, 1% EXAMPLE 1 | | | | | | |
| Pool #1: Enterics | $6.6 \times 10^6$ | <10 | <10 | $4.6 \times 10^6$ | <10 | <10 |
| Pool #2: Pseudomonads | $3.2 \times 10^6$ | <10 | <10 | $3.3 \times 10^6$ | <10 | |
| Pool #3: Staphylococci | $2.0 \times 10^6$ | <10 | <10 | $3.7 \times 10^6$ | <10 | <10 |
| Pool #4: Yeasts | $1.4 \times 10^5$ | <10 | <10 | $4.8 \times 10^5$ | <10 | <10 |
| Pool #5 Mold | $1.9 \times 10^5$ | <10 | <10 | $3.2 \times 10^5$ | <10 | <10 |
| Formulation: Blended Oil Carezomes Preservative: Germazide MPB, 1.5% | | | | | | |
| Pool #1: Enterics | $4.4 \times 10^6$ | <10 | <10 | $3.0 \times 10^6$ | <10 | <10 |
| Pool #2: Pseudomonads | $5.5 \times 10^6$ | <10 | <10 | $1.2 \times 10^6$ | <10 | <10 |
| Pool #3: Staphylococci | $5.5 \times 10^6$ | <10 | <10 | $1.5 \times 10^6$ | <10 | <10 |
| Pool #4: Yeasts | $6.3 \times 10^6$ | <10 | <10 | $7.2 \times 10^6$ | <10 | <10 |
| Pool #5 Mold | $1.9 \times 10^5$ | <10 | 10 | $2.9 \times 10^5$ | <10 | <10 |

TABLE 3-continued

Challenge Tests (CTFA Microbiology Guidelines, M-3, Number of surviving organisms (cfu/g) after DAYS:

| # of Days Organism | 0 Inoc. | 7 Count | 14 Count | 14 Inoc. | 21 Count | 28 Count |
|---|---|---|---|---|---|---|

Pool #1: *Escherichia coli* ATCC #8739, *Kiebsiella pneumoniae* ATCC #13883, *Klebsiella pneumoniae* ATCC #10031, *Enterobacter gergoviae* ATCC #33028, *Emenobacter gergoviae* (in-house isolate)
Pool #2: *Pseudomonas aeruginosa* ATCC #9027, *Pseudomonas stutzeri* ATCC #17588 *Pseudomonas putida* ATCC #49128, *Pseudomonas cepacia* ATCC #25415
Pool #3: *Staphlococcus aureus* ATCC #5538, *Staphlococcus epidermidis* ATCC #12228
Pool #4: *Candida albicans* ATCC #10231, *Candida parapsilosis* ATCC #34136
Pool #5: *Aspargillus niger* ATCC #16404

---

Formulation of Blended oil catezomes ™

40% Mixed sunflower/safflower oil
1.5% Germazide MPB
1% Catemol S-180S
57.5% Water

---

Comparative NR$_{50}$ Values

Merguard 1200, 0.003–0.01%
Potassium sorbate, ~1%
Methyl paraben, 0.055–0.11%
Phenonip, 0.05–0.15%
Propyl Paraben, 0.3–1.0%
Diazoildinyl urea, 0.003–0.01%
Germazide ™ WS, 0.1–0.3%

What is claimed is:

1. A preservative comprising;

approximately forty (40) to eight-five (85) weight percent of phenoxyethanol;

approximately two (2) to forty-eight (48) weight percent of one or more solvents selected from the group consisting of ethanol, propylene glycol, butylene glycol and glycerine;

approximately two (2) to ten (10) weight percent of one or more acids selected from the group consisting of sorbic acid and benzoic acid; and approximately ten (10) to thirty (30) weight percent of chlorophenesin and wherein all percents by weight are based upon the total preservative composition weight.

2. A cosmetic composition comprising up to two (2) percent by weight of the preservative of claim 1; and up to ninety-eight (98) percent by weight of inert non-toxic topically acceptable carrier ingredients suitable for topical application to the skin of a warm-blooded animal, wherein all percents by weight are based upon the total cosmetic composition weight.

3. The preservative of claim 1, wherein said weight percent of phenoxyethanol is sixty (60), said solvent is propylene glycol and said weight percent of propylene glycol is fifteen (15), said acid is sorbic acid and said weight percent of sorbic acid is five (5) and said weight percent of chlorphenesin is twenty (20).

4. The preservative of claim 1 further comprising;
approximately two (2) to ten (10) weight percent of parahydroxybenzoic acid esters (parabens); wherein the solvent is glycerine and the weight percent of glycerine is approximately two to thirty-eight; and wherein all percents by weight are based upon the total preservative composition weight.

5. The preservative of claim 4, wherein said weight percent of phenoxyethanol is fifty-six (56), said weight percent of glycerin is fifteen (15), said acid is benzoic acid and said weight percent of benzoic acid is six (6), said weight percent of chlorphenesin is sixteen (16) and wherein the pharahydroxybenzoic acid ester is methyl paraben and said weight percent of methyl paraben is seven (7).

6. A cosmetic composition comprising
up to two (2) percent by weight of the preservative of claim 4; and
up to ninety-eight (98) percent by weight of inert non-toxic topically acceptable carrier ingredients suitable for topical application to the skin of a warm-blooded animal,
wherein all percents by weight are based upon the total cosmetic composition weight.

* * * * *